US010894143B2

(12) United States Patent
Yokoyama

(10) Patent No.: US 10,894,143 B2
(45) Date of Patent: Jan. 19, 2021

(54) PERCUTANEOUS CATHETER AND METHOD OF USING PERCUTANEOUS CATHETER

(71) Applicant: TERUMO KABUSHIKI KAISHA, Tokyo (JP)

(72) Inventor: Kenji Yokoyama, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 430 days.

(21) Appl. No.: 16/034,578

(22) Filed: Jul. 13, 2018

(65) Prior Publication Data

US 2018/0318547 A1     Nov. 8, 2018

Related U.S. Application Data

(63) Continuation of application No. PCT/JP2016/071856, filed on Jul. 26, 2016.

(30) Foreign Application Priority Data

Jan. 15, 2016   (JP) ................................ 2016-006173

(51) Int. Cl.
    *A61M 25/00*     (2006.01)
    *A61M 39/10*     (2006.01)
    (Continued)

(52) U.S. Cl.
    CPC ........ *A61M 25/003* (2013.01); *A61M 1/1698* (2013.01); *A61M 1/267* (2014.02);
    (Continued)

(58) Field of Classification Search
    CPC .. A61M 25/003; A61M 1/267; A61M 1/1698; A61M 1/3627; A61M 25/005;
    (Continued)

(56) References Cited

U.S. PATENT DOCUMENTS

| 4,333,460 A | 6/1982 | Miller |
| 4,593,687 A | 6/1986 | Gray et al. |

(Continued)

FOREIGN PATENT DOCUMENTS

| CN | 201978220 U | 9/2011 |
| CN | 107405159 A | 11/2017 |

(Continued)

OTHER PUBLICATIONS

Office Action (The First Office Action) dated Jun. 30, 2020, by the State Intellectual Property Office of People's Republic of China in corresponding Chinese Patent Application No. 201680077402.9 and an English Translation of the Office Action. (13 pages).

(Continued)

*Primary Examiner* — Leslie R Deak
(74) *Attorney, Agent, or Firm* — Buchanan Ingersoll & Rooney PC

(57) ABSTRACT

A percutaneous catheter is disclosed through which blood passes. The percutaneous catheter having a catheter tube including a first tube and a second tube, the second tube being in fluid communication with the first tube, the first tube having an inner diameter greater than an inner diameter of the second tube, and wherein the first tube is more flexible than the second tube.

19 Claims, 9 Drawing Sheets

(51) Int. Cl.
*A61M 25/01* (2006.01)
*A61M 1/26* (2006.01)
*A61M 1/16* (2006.01)
*A61M 1/36* (2006.01)
*A61M 25/09* (2006.01)

(52) U.S. Cl.
CPC .......... *A61M 1/3627* (2013.01); *A61M 25/00* (2013.01); *A61M 25/005* (2013.01); *A61M 25/007* (2013.01); *A61M 25/0029* (2013.01); *A61M 25/0068* (2013.01); *A61M 25/0069* (2013.01); *A61M 25/01* (2013.01); *A61M 25/09* (2013.01); *A61M 39/10* (2013.01); *A61M 25/0074* (2013.01); *A61M 2025/0024* (2013.01); *A61M 2025/0031* (2013.01); *A61M 2025/0078* (2013.01); *A61M 2205/3331* (2013.01); *A61M 2210/125* (2013.01)

(58) Field of Classification Search
CPC .. A61M 25/0068; A61M 25/09; A61M 39/10; A61M 25/007
See application file for complete search history.

(56) References Cited

U.S. PATENT DOCUMENTS

| | | | |
|---|---|---|---|
| 5,466,222 | A | 11/1995 | Ressemann et al. |
| 6,929,663 | B2 | 8/2005 | Rioux et al. |
| 2002/0077600 | A1 | 6/2002 | Sirimanne |
| 2005/0107817 | A1 | 5/2005 | White et al. |
| 2007/0213672 | A1 | 9/2007 | Sakai |
| 2007/0293887 | A1 | 12/2007 | Okushi et al. |
| 2009/0071258 | A1 | 3/2009 | Kouda et al. |
| 2009/0088730 | A1 | 4/2009 | Hoofnagle et al. |
| 2013/0110086 | A1 | 5/2013 | Bhagchandani et al. |
| 2016/0220741 | A1 | 8/2016 | Garrison et al. |

FOREIGN PATENT DOCUMENTS

| | | |
|---|---|---|
| EP | 0 161 045 A1 | 11/1985 |
| EP | 0 385 920 A2 | 9/1990 |
| JP | 2007-236666 A | 9/2007 |
| JP | 2008-023318 A | 2/2008 |
| JP | 2012-075547 A | 4/2012 |
| WO | 99/20335 A1 | 4/1999 |
| WO | 2004/093956 A1 | 11/2004 |
| WO | WO 2007-123156 A1 | 11/2007 |

OTHER PUBLICATIONS

The extended European Search Report dated Aug. 9, 2019, by the European Patent Office in corresponding European Patent Application No. 16884980.0-1132. (9 pages).

International Search Report (PCT/ISA/210) dated Oct. 25, 2016, by the Japan Patent Office as the International Searching Authority for International Application No. PCT/JP2016/071856.

Written Opinion (PCT/ISA/237) dated Oct. 25, 2016, by the Japan Patent Office as the International Searching Authority for International Application No. PCT/JP2016/071856.

English translation of the Written Opinion of the International Searching Authority and Search Report dated Oct. 25, 2016 in International Application No. PCT/JP2016/071856.

PERCUTANEOUS CATHETER AND METHOD OF USING PERCUTANEOUS CATHETER

CROSS-REFERENCES TO RELATED APPLICATIONS

This application is a continuation of International Application No. PCT/JP2016/071856 filed on Jul. 26, 2016, which claims priority to Japanese Application No. 2016-006173 filed on Jan. 15, 2016, the entire contents of both of which is incorporated herein by reference.

TECHNICAL FIELD

The present disclosure generally relates to amelioration of a percutaneous catheter feeding blood.

BACKGROUND DISCUSSION

An extracorporeal circulator can be used as a device for temporarily assisting and substituting functions of the heart and lungs until a cardiac function recovers, for example, when the heart of a patient is weak. In the extracorporeal circulator, in order to assist a pumping function of the heart, blood is removed from the vein (vena cava) of a patient via a catheter (tube), and gas exchange in the blood is performed using an artificial lung. After the gas exchange in performed using the artificial lung, the blood returns to the artery (aorta) of the patient via the catheter (tube).

International Publication No. WO2007/123156 A1 discloses a circulation circuit of an extracorporeal circulator.

In a case where blood circulation is performed with the circulation circuit, blood circulates due to a motor and a force generated by a pump driven by the motor.

Therefore, reduction of a pressure loss in a tube constituting the circulation circuit is required.

If the tube has a narrow inner diameter, a pressure loss increases, and the flow rate of water flowing in the circulation circuit decreases. Therefore, unless the inner diameter of the tube has a sufficient inner diameter, a required circulation amount of blood cannot be obtained.

However, if the inner diameter of the tube is increased, the tube can become wider. If the inner diameter of a blood removing catheter (tube) or a blood feeding catheter (tube) to be inserted into the body of a patient is increased, the degree of invasion with respect to the body of the patient increases, so that a load with respect to the body of the patient increases.

Pressure loss can be determined based on the cross-sectional area of a passage of a tube times (×) the length of the tube.

Therefore, a pressure loss can be reduced by reducing the wall thickness of the tube.

The wall thickness of a tube used in an extracorporeal circulator can be reduced. However, if the wall thickness is further reduced, a risk such as a rupture of the wall of the tube increases when the tube is in use, such that it is difficult to further reduce the wall thickness of the tube.

SUMMARY

A percutaneous catheter is disclosed, which can reduce a pressure loss of a liquid circulating in a circuit and can help ensure a required flow rate of the liquid without increasing invasion or a load with respect to the body of a patient, and a method of using a percutaneous catheter.

According to the present disclosure, a percutaneous catheter is disclosed through which blood passes. The percutaneous catheter is provided with a catheter tube that includes a first tube and a second tube communicating with the first tube. The first tube has an inner diameter greater than an inner diameter of the second tube and the first tube has a structure more flexible than the second tube.

According to an embodiment, the wider the inner diameter of the first tube, the larger the cross-sectional area of a passage. Accordingly, a pressure loss decreases and a liquid feeding amount increases. In this case, since the first tube is highly flexible (i.e., possesses relatively high flexibility), when the first tube is inserted into a blood vessel of a patient, the dilator is inserted through the first tube, which causes the first tube to expand in an axial direction (i.e., length direction). In this state, as much as the first tube has expanded in the length direction, the outer diameter of the tube becomes smaller (i.e., narrower). Therefore, a load applied to a blood vessel of a patient at the time of insertion can be reduced, thereby being a relatively low invasive procedure. After insertion, if the dilator is withdrawn, the first tube returns to the original state from the expanded state and has a wide cross-sectional area, so that a pressure loss can be reduced as described above.

In accordance with an exemplary embodiment, a distal tip gradually reduced in diameter toward a distal side is fixed to a distal end of the first tube, a proximal end of the first tube and the second tube are connected to each other by a connector having a side hole, and the distal tip is provided with a blood removing hole and internally has a flat butting portion such that a distal portion of a dilator used at a time of insertion is received in a planar manner.

According to an embodiment, when the catheter is inserted into a blood vessel of a patient, if the catheter is elongated in the axial direction (or length direction) using the dilator as described above, the outer diameter becomes narrow. In a case where the first tube has a narrow outer diameter, at the time of invasion, even if the first tube is inserted from a thin vascular part, the first tube can be inserted in a low invasive manner. After insertion, the first tube invades the body deeply. For example, in a case of a catheter for blood removing, the first tube is disposed deep inside from a location in the vicinity of the abdomen of a patient. In this way, since the first tube is disposed inside a relatively wide blood vessel of the body of the patient, even if the first tube is wide at the time of liquid feeding, a load with respect to the body of the patient does not increase to a relatively harmful degree. Moreover, in the vicinity of a site where the first tube is disposed inside the body, since there is a small risk of a kink of the tube, even if the first tube is formed of a soft material, there is relatively no inconvenience.

Moreover, in the distal tip, when the dilator is used at the time of insertion of the catheter, the flat distal end of the dilator presses the flat butting portion of the distal tip in a planar manner. Accordingly, when the dilator is removed (or pulled out) after insertion, the dilator can effectively be prevented from being caught by the inner side of the soft first tube, and the first tube is not disposed in a distorted manner.

Preferably, the first tube is reinforced with a wire so as to realize a structure which is not blocked due to action of a negative pressure applied to the first tube, and even when the first tube expands and contracts, the wire is configured to be able to follow the expansion and contraction of the first tube.

According to an embodiment, if the first tube has a reduced wall thickness, if the first tube is reinforced with the wire, the first tube is unlikely to be damaged. In this case, for example, a wire having a meshed shape or a coiled shape can be used.

In accordance with an exemplary embodiment, two divided lumens which are hollow liquid passing passages are formed inside the second tube, a first lumen which is one liquid passing passage serving as a blood feeding path extends inside the first tube, and a second lumen which is a remaining liquid passing passage serving as a blood removing path is connected to a blood feeding hole which is the side hole of the connector.

According to an embodiment, both blood removing and liquid (i.e., blood) feeding can be performed with one catheter.

In accordance with an exemplary embodiment, the distal tip can be formed of a hard material having a tapered shape, the distal tip being fixed to the distal end of the first tube, and a flat receiving surface attached to a distal plane of the dilator used prior to insertion of the catheter can be formed on an inner side of the distal tip.

According to an embodiment, since a hard distal tip is fixed to a relatively soft distal end of the first tube, it is possible to prevent inconvenience in which the first tube is bent at the time of insertion of the catheter. Furthermore, at the time of the insertion, the dilator can appropriately press the distal tip without inclination. When the dilator is pulled out, if the distal end of the dilator is flat, wrinkling (i.e., distortion of the first tube) generated due to the dilator being caught by the inner surface of the soft first tube can be prevented.

According to the present disclosure, a method is disclosed of using a percutaneous catheter through which blood passes, the catheter being provided with a catheter tube that includes a first tube and a second tube communicating with the first tube, the first tube having an inner diameter greater than an inner diameter of the second tube, and the first tube having a structure more flexible than the second tube. The method of using a percutaneous catheter can include inserting a dilator with respect to the catheter, causing the first tube to expand, and causing an outer diameter of the first tube to be in a narrow state; and then inserting the percutaneous catheter along a guide wire which has been previously been inserted with respect to a catheter insertion site of a patient.

According to an embodiment, in the catheter of the present disclosure, the wider the inner diameter of the first tube, the larger the cross-sectional area of a passage. Accordingly, in a catheter having a larger cross-sectional area, pressure loss can be decreased (or reduced) and a liquid feeding amount can be increased. In accordance with an exemplary embodiment, since the first tube can be highly flexible, when the first tube is inserted into a blood vessel of a patient, the dilator is inserted through the first tube, which expands in an axial direction (i.e., length direction). Therefore, the first tube can be inserted into the body of a patient in a relatively low invasive manner.

In accordance with an exemplary embodiment, the method of using a percutaneous catheter can include pulling the dilator and the guide wire to a location of a clamping tube of the percutaneous catheter with respect to each of the percutaneous catheters and clamping the dilator and the guide wire after each of the catheters for blood feeding and blood removing is inserted, and connecting a circulation circuit of an extracorporeal circulator to each of the connectors of the percutaneous catheters.

According to an embodiment, since the catheter is clamped before the dilator and the guide wire are completely withdrawn, blood does not leak out when the catheter is connected to the extracorporeal circulator.

In accordance with an exemplary embodiment, the method of using a percutaneous catheter further includes removing an air bubble remaining inside each of the connectors of the catheters by using a syringe from the circulation circuit side, after the connection.

According to an embodiment, an air bubble can be effectively prevented from entering a blood vessel of a patient through the circulation circuit.

As described above, the present disclosure is capable of reducing a pressure loss of a liquid circulating in a circuit and ensuring a required flow rate of the liquid without increasing invasion or a load with respect to the body of a patient.

DESCRIPTION OF EMBODIMENTS

Hereinafter, preferable embodiments of the present disclosure will be described in detail with reference to the drawings.

The embodiments described below are examples of the present disclosure, and the embodiments are subjected to various limitations, which are technically preferable. However, the scope of the present disclosure is not limited to the aspects of the disclosure unless otherwise stated in the following description particularly limiting the present disclosure.

Figure 1:
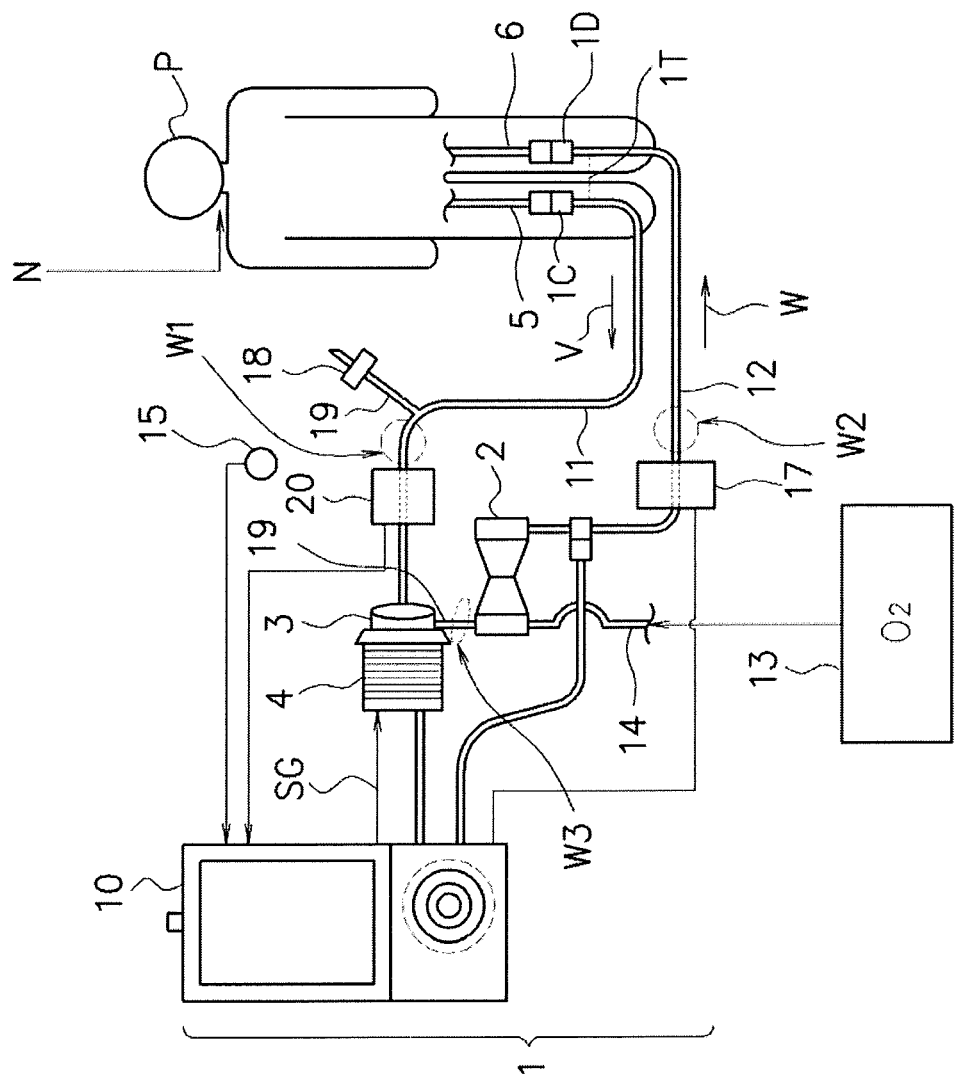
FIG. 1 is a system diagram illustrating an example of an extracorporeal circulator in which an embodiment of a percutaneous catheter of the present disclosure is applied.

FIG. 1 is a system diagram illustrating an example of an extracorporeal circulator in which an embodiment of a percutaneous catheter of the present disclosure is applied and which can be used as a device, for example, for percutaneous cardiopulmonary support (PCPS), for temporarily assisting and substituting functions of the heart and lungs until a cardiac function recovers, for example, when the heart of a patient is relatively weak.

In FIG. 1, a pump of an extracorporeal circulator 1 is operated to remove blood from the vein (vena cava) of the patient, and the blood is oxygenated by exchanging gas in the blood through an artificial lung. After removing the blood from the vein of the patient, artificial lung extracorporeal blood circulation can be performed through which the blood returns to the artery (aorta) of the patient. The extracorporeal circulator 1 is a device for assisting the heart and lungs.

As illustrated in FIG. 1, the extracorporeal circulator 1 has a circulation circuit 1R which causes blood to circulate. The circulation circuit 1R includes an artificial lung 2, a centrifugal pump 3, a drive motor 4 which is a driving means for driving (i.e., drives) the centrifugal pump 3, a vein side catheter (percutaneous catheter for blood removing) 5, an artery side catheter (catheter for blood feeding) 6, and a controller 10 which serves as a control unit.

As illustrated in FIG. 1, the vein side catheter (catheter for blood removing) 5 is inserted through the femoral vein, and a distal end of the vein side catheter 5 indwells in the right atrium. The artery side catheter (catheter for blood feeding) 6 is inserted through the femoral artery. The vein side catheter 5 is connected to the centrifugal pump 3 using a blood removing tube (also referred to as a blood removing line) 11. The blood removing tube 11 is a conduit line for sending blood.

When the drive motor 4 operates the centrifugal pump 3 in response to a command signal (SG) of the controller 10, the centrifugal pump 3 removes blood through the blood removing tube 11 and causes the blood to pass through the artificial lung 2. After the blood passes through the artificial lung 2, the centrifugal pump 3 can cause the blood to return to a patient (P) via a blood feeding tube 12 (also referred to as a blood feeding line).

In accordance with an exemplary embodiment, the artificial lung 2 can be disposed (or arranged) between the centrifugal pump 3 and the blood feeding tube 12. The artificial lung 2 performs a gas exchange operation (oxygenation and/or carbon dioxide removal) with respect to the blood removed from the patient. The artificial lung 2 is a membrane-type artificial lung, for example. It is particularly preferable, for example, to use a hollow fiber membrane-type artificial lung. Oxygen gas is supplied to the artificial lung 2 from an oxygen gas supply section 13 through a tube 14. The blood feeding tube 12 is a conduit line connecting the artificial lung 2 and the artery side catheter 6 to each other.

The conduit lines of the blood removing tube 11 and the blood feeding tube 12 can be made of synthetic resin, for example, vinyl chloride resin or silicone rubber which is highly transparent and flexible to be elastically deformable (will be described below in detail). Blood (liquid) flows as illustrated in FIG. 1 in a V-direction inside the blood removing tube 11, and blood flows in a W-direction inside the blood feeding tube 12.

In the example of the circulation circuit 1R illustrated in FIG. 1, an ultrasound air bubble detection sensor 20 can be disposed outside the blood removing tube 11 in a middle part of the blood removing tube 11. A fast clamp (i.e., a device for closing or shutting off a blood tube in a relatively quick manner) 17 is disposed outside the blood feeding tube 12 in an intermediate position of the blood feeding tube 12.

In a case where the ultrasound air bubble detection sensor 20 detects that an air bubble is present in the blood being sent to the inside of the blood removing tube 11, the ultrasound air bubble detection sensor 20 transmits a measurement signal of air bubble detection to the controller 10. Accordingly, the fast clamp 17 can quickly (or urgently) close the blood feeding tube 12 in response to a command of the controller 10 in order to stop blood from being sent to the patient P side.

In the ultrasound air bubble detection sensor 20, in a case where an air bubble is incorporated into a circuit due to an erroneous operation of a three-way stopcock 18, damage to the tube, or the like during a blood circulation operation, the incorporated air bubble can be detected. If an air bubble is detected, the controller 10 in FIG. 1 can sound an alarm for notification. Accordingly, the rotational frequency of the centrifugal pump 3 can be reduced. Alternatively, the centrifugal pump 3 can be stopped. Moreover, the controller 10 commands the fast clamp 17 such that the fast clamp 17 immediately closes the blood feeding tube 12. For example, an air bubble can be stopped from being sent to the inside of the body of the patient P. A circulation operation of blood in the circulation circuit 1R of the extracorporeal circulator 1 can be suppressed or can be temporarily halted by performing all the control or a part of an operation described above to help prevent an air bubble from being incorporated into the body of the patient P.

A pressure sensor can be provided in any location of the tube of the circulation circuit 1R of the extracorporeal circulator 1 illustrated in FIG. 1. The pressure sensor can be, for example, preferably mounted in the tube 11 (12, 19). Accordingly, when the extracorporeal circulator 1 performs an extracorporeal circulation operation with respect to the patient P, the pressure sensor (not illustrated) can measure the intra-circuit pressure during blood circulation through the inside of the tube 11 (12, 19). The pressure sensor can be mounted in any one or all of a mounting position W1 in a middle part of the blood removing tube 11 of the circulation circuit 1R, a mounting position W2 in a middle part of the blood feeding tube 12 of the circulation circuit 1R, and a mounting position W3 in a middle part of a connection tube 19 which connects the centrifugal pump 3 and the artificial lung 2 to each other.

First Embodiment

Figure 2:
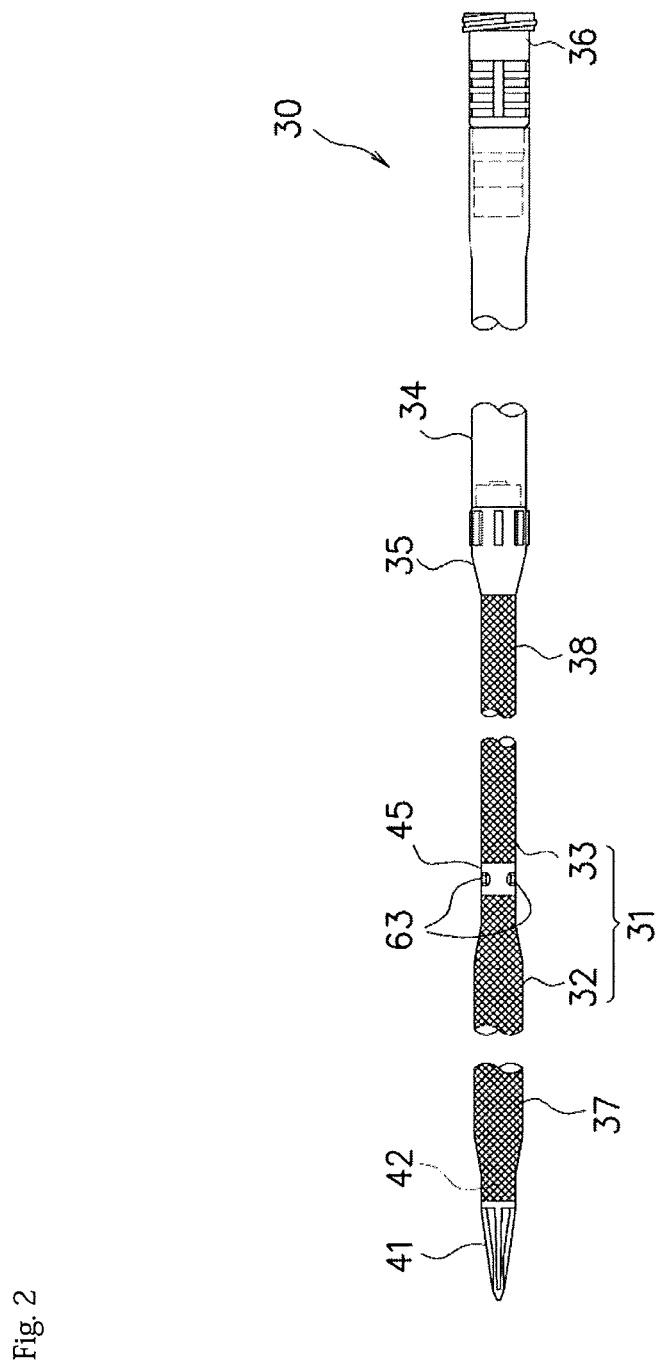
FIG. 2 is a side view according to a first embodiment of a percutaneous catheter of the present disclosure.
Figure 3:
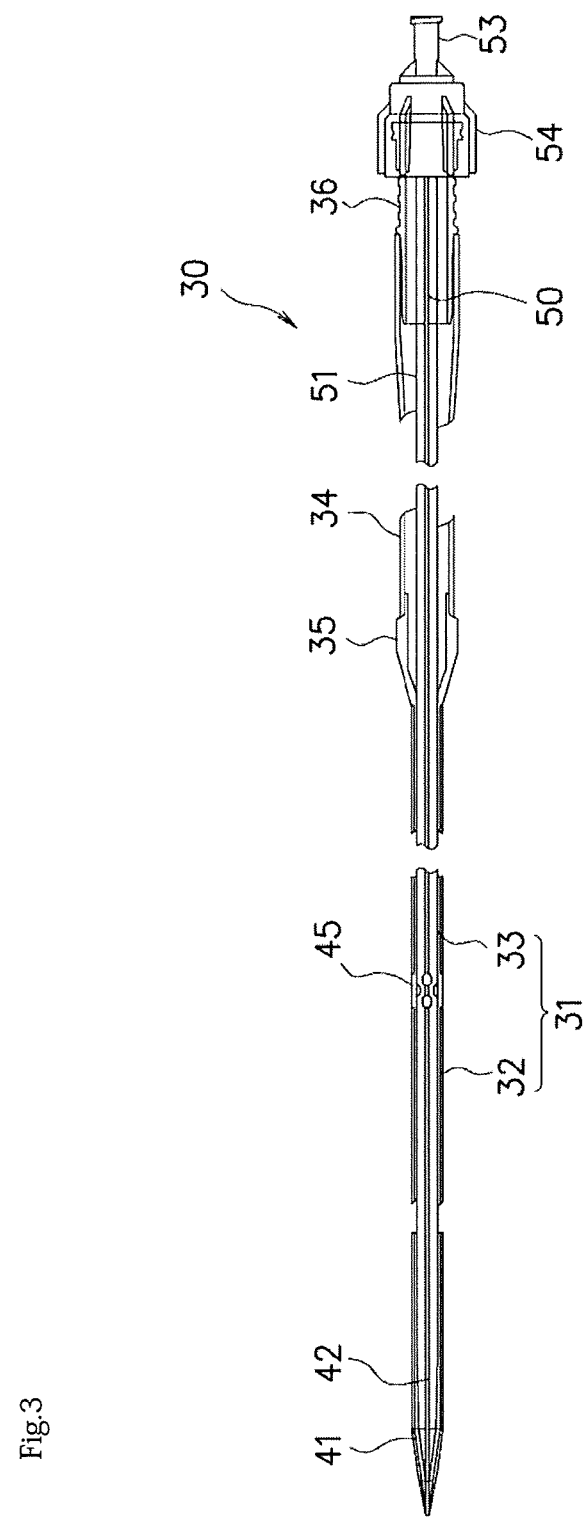
FIG. 3 is a schematic cross-sectional view of FIG. 2.

With reference to FIGS. 2 and 3, a first embodiment of a percutaneous catheter of the present disclosure (which will hereinafter be referred to as a "catheter") will be described. FIG. 2 is a front view of the catheter of the first embodiment. FIG. 3 is a schematic cross-sectional view of the catheter of FIG. 2. FIG. 3 illustrates a set dilator used when the catheter is inserted. The catheter is used for removing blood, as the vein side catheter (catheter for blood removing) 5 in FIG. 1.

In FIGS. 2 and 3, a catheter 30 has a catheter tube 31. The catheter tube 31 includes a first tube 32 and a second tube 33 communicating (i.e., in fluid communication with) the first tube 32.

The first tube 32 has an inner diameter, which is greater (or wider) than an inner diameter of the second tube 33. Furthermore, the first tube 32 has a structure, such that the first tube 32 is more flexible than the second tube 33.

A distal tip 41 is fixed to the distal end of the first tube 32 via a distal connector 42, as illustrated in FIGS. 2 and 3. The distal tip 41 has a tapered shape such that the distal tip 41 gradually reduces in diameter toward the distal side.

A proximal end of the first tube 32 and the distal end of the second tube 33 are connected to each other by a connector 45 having a side hole. The structures of the connector 45 and the distal tip 41 will be described below in detail.

In FIGS. 2 and 3, a proximal side of the catheter 30 is connected to a clamping tube 34, which is formed of a soft material (for example, a resin tube made of polyvinyl chloride), via a catheter connector 35. As illustrated in FIG. 3, a hollow dilator tube 51 internally equipped with a lock connector 36 is attached to the clamping tube 34. A hub 53 is attached to the lock connector 36 together with a screw ring 54 by utilizing a male screw provided on the proximal side of the lock connector 36.

The hub 53 has a dilator 50 utilized when the catheter 30 is inserted as described below. In accordance with an exemplary embodiment, the dilator 50 can be an extremely thin wire material. The dilator 50 can be internally mounted inside the dilator tube 51 over an entire length of a center portion of the catheter 30. The dilator 50 can be guided by a guide wire (not illustrated) and plays a role in widening a narrow blood vessel when the catheter 30 is inserted (i.e., when the dilator is inserted into the catheter, the catheter with the dilator obtains a stiffness sufficient to widen or enlarge a blood vessel). As described below, the dilator 50 is withdrawn by pulling out the hub 53 after the catheter has been inserted into the blood vessel.

The inside of the catheter 30 is hollow (lumen) as a passage for a liquid. In FIGS. 2 and 3, the distal side (left side in the diagram) beyond the catheter connector 35 of the catheter 30 is the catheter tube 31 in which the liquid passage is provided. In the present embodiment, the first tube 32 and the second tube 33 have structures different from each other at the part of the connector 45 with a side hole in the catheter tube 31. However, the first tube 32 and the second tube 33 form a single lumen as the liquid passage.

In accordance with an exemplary embodiment, an inner diameter of the first tube 32 is wider (or greater) than an inner diameter of the second tube 33. In accordance with an exemplary embodiment, since the first tube 32 has a larger inner diameter than the inner diameter of the second tube 33, a pressure loss in the catheter 30 can be reduced by partially widening the liquid passage, for example, for the length of the first tube 32. The inner diameter of the first tube 32 can be widened because the first tube 32 is inserted into a blood vessel of a patient deeper than the position where the second tube 33 is disposed. Each of the lengths of the first tube 32 and the second tube 33 can be set such that the first tube 32 can receive right cardiac blood and the second tube 33 can receive venous blood from the inferior vena cava.

In accordance with an exemplary embodiment, the first tube 32 can be positioned at the inferior vena cava and the second tube 33 can be positioned at the femoral vein, so that the first tube 32 can have a partially widened liquid passage (i.e., inner diameter) and a pressure loss can be reduced. In accordance with an exemplary embodiment, the second tube 33 can have the length of the femoral vein. As an actual length, for example, the first tube 22 can be, for example, approximately 20 cm to 40 cm, and the length of the second tube 33 can be, for example, approximately 20 cm to 30 cm.

In accordance with an exemplary embodiment, since the first tube 32 has an inner diameter that is greater than an inner diameter of the second tube 33, a pressure loss decreases in a route corresponding to the length of the first tube 32.

In accordance with an exemplary embodiment, for example, a pressure loss of the catheter 30 becomes the product of the entire length of the catheter 30 times the cross-sectional area (average) of the passage of the catheter 30 as illustrated in FIGS. 2 and 3.

Figure 12:
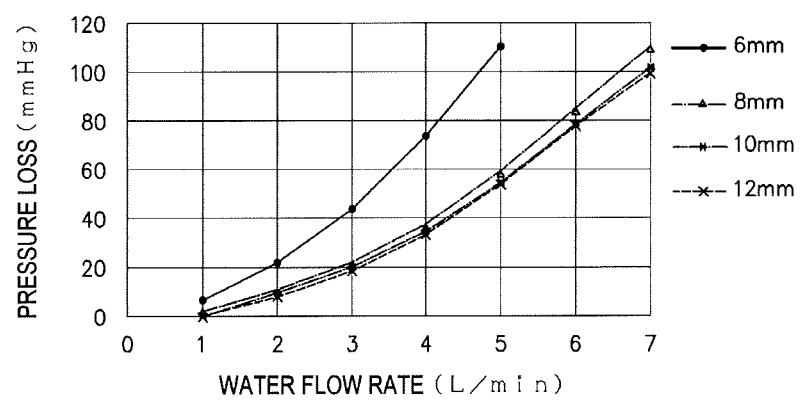
FIG. 12 is a graph illustrating an example of a pressure loss (vertical axis) and a water flow rate (horizontal axis) corresponding to an inner diameter of a tube forming a liquid passage.

Here, FIG. 12 is a graph illustrating an example of a pressure loss (vertical axis) and a water flow rate (horizontal axis) corresponding to an inner diameter of a tube.

As illustrated, if the tube has a narrow inner diameter, a pressure loss increases, and the flow rate of water flowing in the circulation circuit decreases. Therefore, unless the inner diameter of the tube has a sufficient inner diameter, a required circulation amount of blood cannot be obtained. In addition, the inner diameter of the first tube varies depending on the inner diameter of the second tube.

FIG. 12 illustrates a pressure loss in an example having the following conditions.

The length unit (6 mm) indicates a pressure loss in an example where the first tube 32 has an inner diameter of 6 mm and a length of 20 cm, and a pressure loss in a case where the second tube 33 has an inner diameter of 6 mm and a length of 30 cm.

In addition, the length unit (8 mm) indicates a pressure loss when the first tube 32 has an inner diameter of 8 mm and a length of 20 cm, and a pressure loss when the second tube 33 has an inner diameter of 6 mm and a length of 30 cm.

In addition, the length unit (10 mm) indicates a pressure loss when the first tube 32 has an inner diameter of 10 mm and a length of 20 cm, and a pressure loss when the second tube 33 has an inner diameter of 6 mm and a length of 30 cm.

In addition, the length unit (12 mm) indicates a pressure loss when the first tube 32 has an inner diameter of 12 mm and a length of 20 cm, and a pressure loss when the second tube 33 has an inner diameter of 6 mm and a length of 30 cm.

Specifically, in regard to a using catheter, for example, in a case of a blood removing catheter having the outer diameter (Fr) of 21Fr (the outer diameter×the inner diameter: 7 mm×6 mm), as illustrated in FIG. 12, a pressure loss could be sufficiently reduced and the required flow rate could be obtained when the inner diameter of the first tube is 8 mm or greater.

The material from which the catheter tube 31 can be fabricated can include silicon, polyethylene, nylon, urethane, polyurethane, fluororesin, thermoplastic elastomer resin, and the like which have been used in the related art, or by using a composite material of the materials. The catheter tube 31 can be formed through extrusion molding, for example, using the materials described above.

Since the first tube 32 and the second tube 33 are separate bodies, the first tube 32 and the second tube 33 can each be formed of a different material or by a different molding method.

For example, a silicon raw material has a relatively high biocompatibility and the raw material of silicon is soft as well, thereby having an advantage that a blood vessel is unlikely to be damaged by the catheter tube 31. A polyethylene raw material is soft and has rigidity to withstand a pressure. Furthermore, a polyethylene raw material has biocompatibility equal to that of a silicon raw material. A polyethylene raw material has an advantage of being harder than silicon and can be relatively easily inserted into a narrow blood vessel. In addition, a polyurethane raw material has an advantage of becoming soft after insertion.

As a material of the tube, an applicable material is used by utilizing the advantages of the raw materials.

In addition, a polyurethane raw material may be subjected to hydrophilic coating. In this case, the surface of the tube becomes smooth, the tube is relatively easily inserted into a blood vessel, and a vascular wall is unlikely to be damaged. In addition, blood or protein is unlikely to be attached to the surface of tube, and it is possible to expect that a thrombus can be prevented from being formed.

From the viewpoint described above, in the present embodiment, it is preferable that the first tube 32 has excellent flexibility. For example, the first tube 32 can be formed of silicon.

In addition, since the material from which the first tube 32 is made is a relatively soft material, and a hard distal tip 41 is fixed to a distal portion of the first tube 32, squashing (i.e., the deformation of the first tube 32 by vacuum pressure at the time of blood removing) of the first tube 32 at the time of blood removing can be effectively avoided.

Since the second tube 33 is disposed at the inferior vena cava of a patient, the inner diameter of the second tube 33 may be same as that in the related art, and the hardness of the second tube 33 may be the same as that in the related art. Therefore, for example, the second tube 33 can be formed by using the materials and a manufacturing method in the related art.

In accordance with an exemplary embodiment, a relatively soft material which is more flexible than the second tube 33 can be suitably selected for the first tube 32 from the materials described above. The first tube 32 is at a relatively deep position (right cardiac blood) after insertion of the catheter. Since a blood vessel is wide at that position, there is little risk of a kink in the first tube 32. Therefore, the inner diameter of the first tube 32 can be set to be wider than that of a blood removing catheter in the related art. In this case, the inner diameter of the first tube 32 can be determined based on the graph in FIG. 12. For example, the inner diameter of the first tube 32 can be set such that the average inner diameter of the liquid passage over the entire length of the catheter 30 becomes 8 mm or larger. Accordingly, a required liquid feeding amount can be obtained. In addition, the upper limit value for the inner diameter of the first tube 32 may be determined based on the size limit (i.e., upper limit) in consideration of invasiveness with respect to the body of a patient. In the present embodiment, the inner diameter of the first tube 32 can be set to 9 mm, for example.

As can be understood from FIG. 2, each of the distal portion and the rear end portion of the first tube 32 can be formed (or fabricated) to be a relatively thin portion which is gradually thinned (reduced) so as to be connected to the second tube 33 having an inner diameter of 6 mm.

Next, a reinforcing structure of the catheter tube 31 will be described.

In accordance with an exemplary embodiment, at least the first tube 32, and preferably both the first tube 32 and the second tube 33 are reinforced by a wire material.

In this case, the wire has a meshed shape or a coiled shape, and a metal wire or a resin wire can be used.

In an exemplary embodiment, for example, wire meshes 37 and 38 formed of a thin stainless steel wire are used. Furthermore, in the wire meshes 37 and 38, meshes are disposed on a surface of the material of the tube described above and are subjected to resin coating, so that fixing properties and followability are enhanced.

In this embodiment, as illustrated in FIG. 1, the wire mesh 37 is disposed on a surface of the highly flexible first tube 32, and an urethane coating is placed on the wire mesh 37 and the first tube 32. Accordingly, the wire mesh 37 is firmly fixed to the surface of the first tube 32. Therefore, when the first tube 32 expands, reticulations of the wire mesh 37 are opened while following the surface of the first tube 32. Accordingly, it is possible to effectively prevent damage or the like of the first tube 32.

Figure 4:
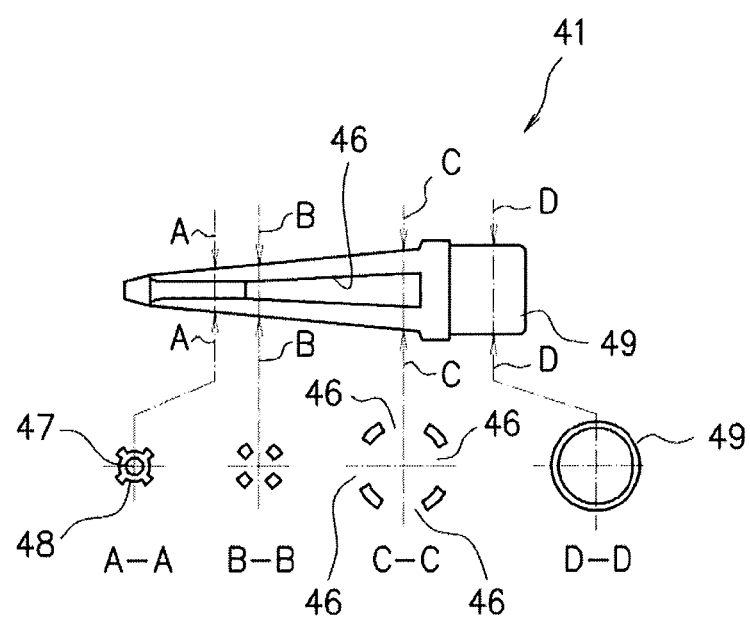
FIG. 4 is a front view illustrating an example of a distal tip and a cut end surface view of each portion of the distal tip.
Figure 5:
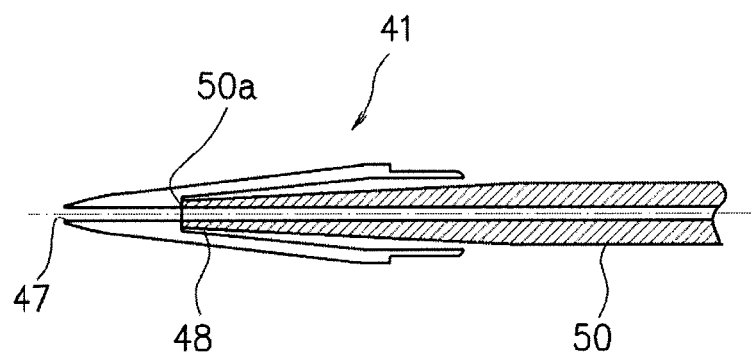
FIG. 5 is an enlarged schematic cross-sectional view illustrating a state where a dilator is inserted into the distal tip in FIG. 4.

FIG. 4 is a front view illustrating an example of a distal tip 41 and a cut end surface view of each portion of the distal tip 41. FIG. 5 is an enlarged schematic cross-sectional view illustrating a state where a dilator 50 is inserted into the distal tip 41 in FIG. 4.

In the diagrams, the distal tip 41 is fixed to the distal end of the first tube 32. As illustrated in FIG. 4, the distal tip 41 has a tapered shape gradually reduced in diameter toward the distal end (or left side of FIG. 4) and has a substantially conical shape. For example, the distal tip 41 can be a molded product made of rigid plastic.

As illustrated in FIG. 4, a base portion 49 of the slender conical-shaped distal tip 42 is inserted into the distal end of the first tube 32 in FIG. 1 and is fixed to the first tube 32. The inside of the distal tip 41 communicates with the liquid passage of the first tube 32. A plurality of penetrated side surface holes 46 are formed on a side surface of the distal tip 42. A plurality of through-holes 47 can also be provided in the distal portion of the distal tip 42. In accordance with an exemplary embodiment, the plurality of through-holes 47 functions as blood removing holes.

As illustrated in FIG. 5, a flat receiving surface 48 attached to a distal plane 50a of the dilator 50 used prior to insertion of the catheter is formed on an inner side of the distal tip 41.

Thus, in a case where the first tube 32 has a narrow outer diameter, at the time of invasion, even if the first tube 32 is inserted from a thin vascular part, the first tube 32 can be inserted in a relatively low invasive manner. After insertion, the first tube 32 invades the body deeply. Since the catheter 30 is a catheter for blood removing, the first tube 32 is disposed deep inside from a location in the vicinity of the abdomen of a patient. Accordingly, the first tube 32 is disposed inside a relatively wide blood vessel of the body of the patient. Therefore, a load with respect to the body of the patient can be relatively light. Moreover, in the vicinity of a site where the first tube is disposed inside the body, since there is a relatively small risk of kinking of the first tube 32, even if the first tube 32 is formed of a soft material, there is no inconvenience to the patient.

Moreover, in the distal tip 41, the dilator 50 can be used at the time of insertion of the catheter 30. In this case, the distal end of the dilator 50 can have a flat surface 50a. Accordingly, when the dilator 50 is pulled out after insertion of the catheter 30, the dilator 50 is effectively prevented from being caught by the inner side of the soft first tube 32, and the first tube 32 is not disposed in a distorted manner.

Figure 6:
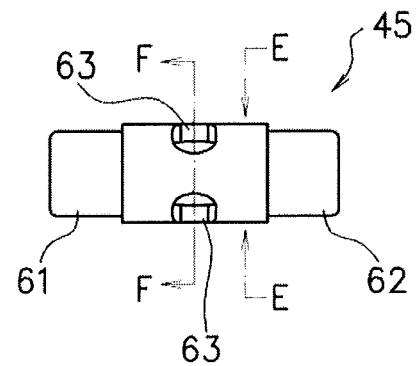
FIG. 6 is a front view illustrating an example of a connector with a side hole.

FIG. 6 illustrates the side hole connector 45. The side hole connector 45 is a joint member connecting the first tube 32 and the second tube 33 to each other. The side hole connector 45 has a tubular body in its entirety and can be, for example, a molded product made of a hard plastic, for example.

Figure 7:
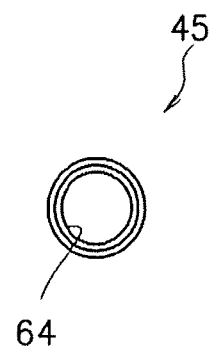
FIG. 7 is an end surface view cut along E-E in FIG. 6.
Figure 8:
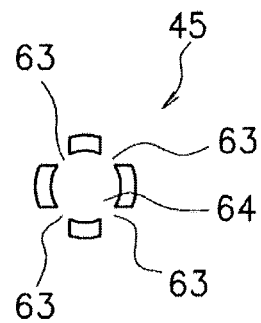
FIG. 8 is an end surface view cut along F-F in FIG. 6.

The side hole connector 45 has connection sections 61 and 62 which are decreased diameter portions in both end portions of the tubular body. When the connection section of the side hole connector 45 is pushed (or stuck) into a counterpart tube, a liquid passage 64 of the side hole connector 45 as shown in FIG. 7 communicates with the tube (or lumen) of the counterpart tube. As illustrated in FIG. 8, the side hole connector 45 has a plurality of through-holes 63, 63, 63, and 63 which are open on a side surface. The through-holes 63, 63, 63, and 63 (side holes) function as the blood removing holes.

In addition, as illustrated in FIG. 2, the first tube 32 and the second tube 33 are connected to each other by the side hole connector 45. Furthermore, the hard distal tip 41 is fixed to the distal end of the first tube 32. Accordingly, in the soft first tube 32, when a negative pressure functions in the extracorporeal circulator in FIG. 1, the first tube 32 is effectively prevented from being squashed and blocked.

Method of Using Catheter

FIG. 2 illustrates a preparation stage before the catheter 30 is inserted, as described.

In accordance with an exemplary embodiment, first, the dilator 50 is inserted with respect to the catheter 30. The dilator 50 passes through the dilator tube 51 and enters the distal tip 41 via the second tube 33 and then the first tube 32. As illustrated in FIG. 5, the dilator 50 is attached to the flat receiving surface 48 of the distal tip 42.

Accordingly, the inserted dilator 50 causes the soft first tube 32 to expand or extend in an axial direction. At the same time, as shown in FIG. 3, the outer diameter of the first tube 32 is in a narrowed state (i.e., having a reduced or smaller outer diameter).

Subsequently, the catheter 30 is inserted with respect to a catheter insertion site (i.e., site for transdermal insertion of the catheter) of a patient along the guide wire (not illustrated) which has been inserted in advance of the catheter 30.

After the catheter 30 is inserted, the dilator 50 and the guide wire are pulled to a location of the clamping tube 34 of the catheter 30 with respect to the catheter 30, and the catheter 30 is clamped by using forceps (not illustrated). The circulation circuit of the extracorporeal circulator in FIG. 1 is connected to the catheter connector 35.

After connection, air bubbles remaining inside the connector of the catheter 30 are removed from the circulation circuit side by using a syringe (not illustrated).

Thus, the wider the inner diameter of the first tube 32, the larger the cross-sectional area of the passage. Accordingly, with the increased inner diameter of the first tube, a pressure loss decreases and a liquid feeding amount increases. In this case, since the first tube 32 is highly flexible, when the first tube 32 is inserted into a blood vessel of a patient, the dilator 50 is inserted through the first tube 32, which expands in a length direction (or axial direction). Therefore, the catheter 30 can be inserted into the body of a patient in a relatively low invasive manner.

In addition, since the clamping tube 34 can be clamped before the dilator 50 and the guide wire are completely withdrawn, blood can be prevented from leaking out when the catheter 30 is connected to the extracorporeal circulator. Therefore, air bubbles can be effectively prevented from entering a blood vessel of a patient through the circulation circuit.

Second Embodiment

Figure 9:
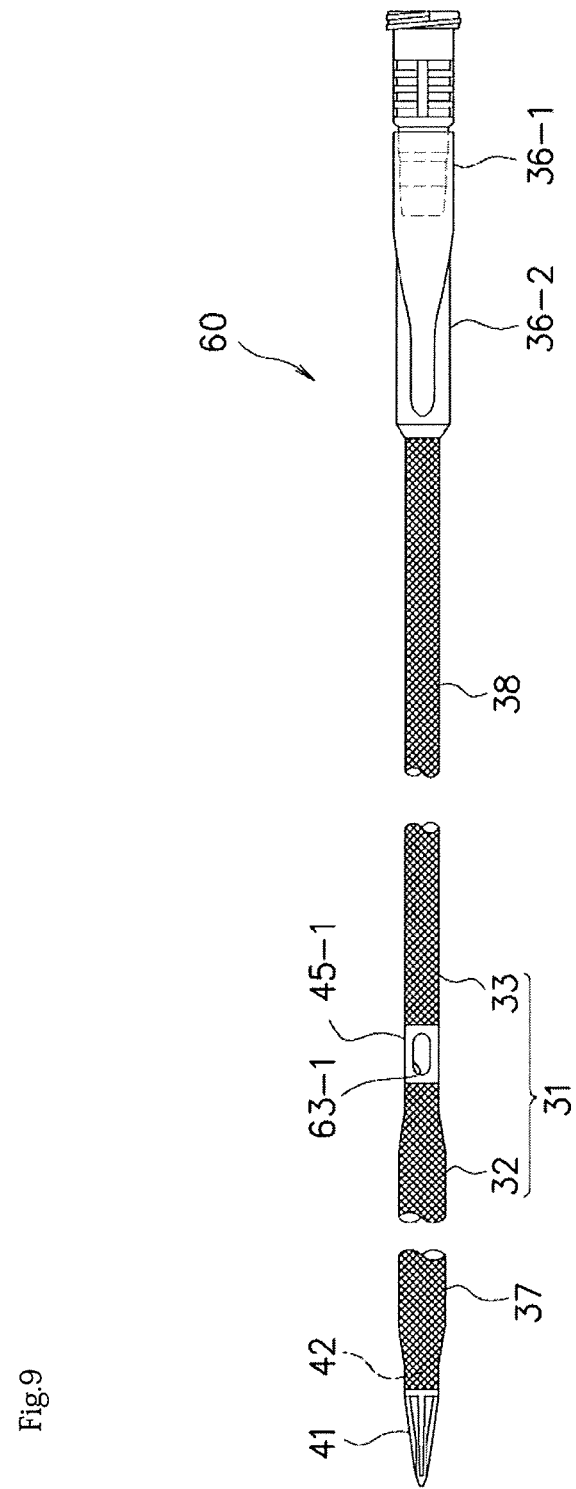
FIG. 9 is a plan view according to a second embodiment of a percutaneous catheter of the present disclosure.
Figure 10:
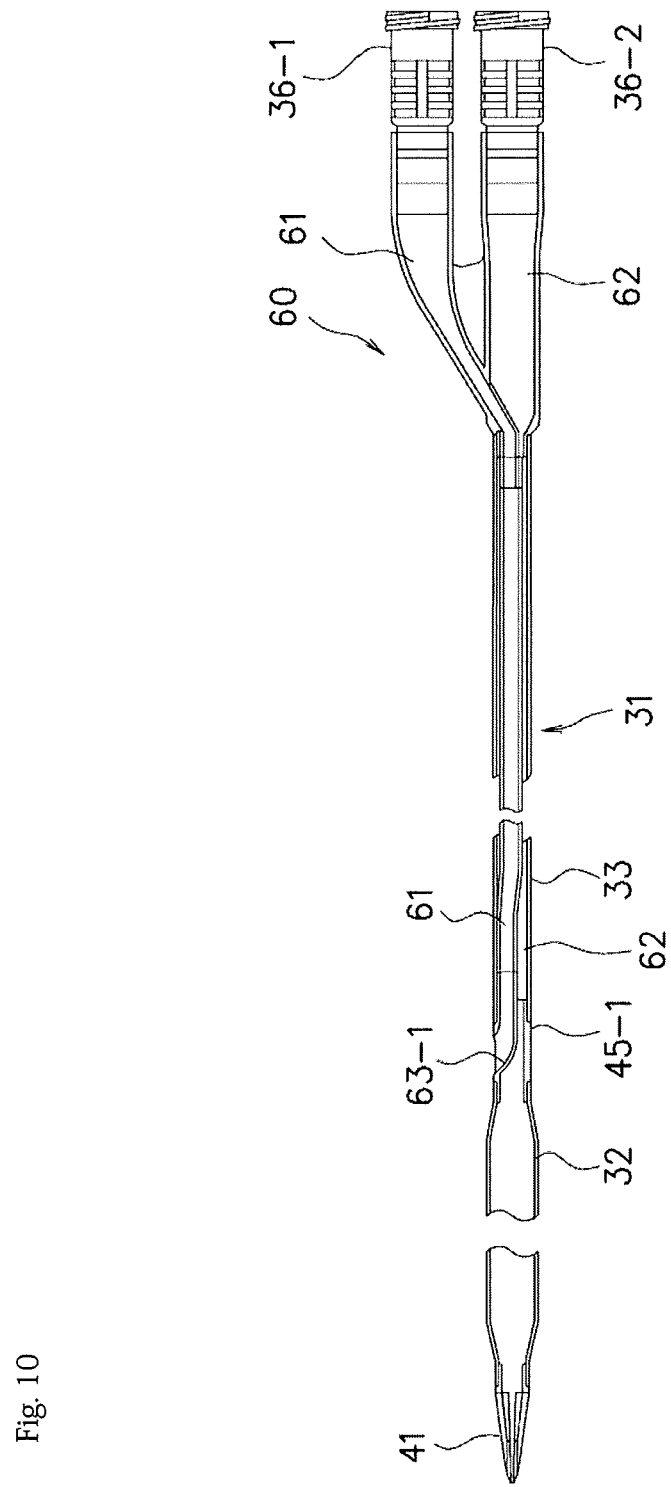
FIG. 10 is a schematic cross-sectional view of the percutaneous catheter in FIG. 9 seen from a side surface.
Figure 11:
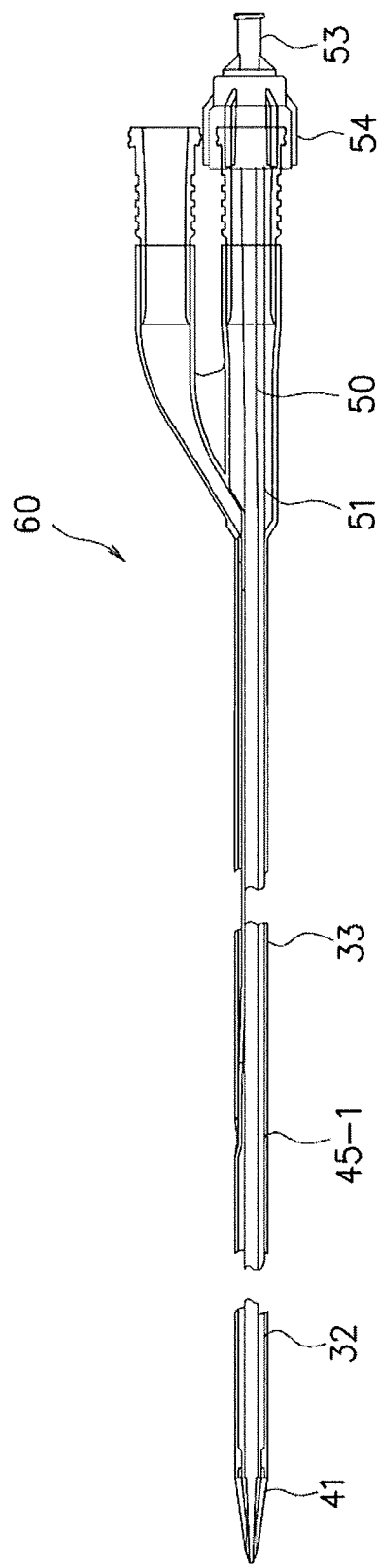
FIG. 11 is a schematic cross-sectional view illustrating a state where the dilator is inserted into the percutaneous catheter in FIG. 10.

With reference to FIGS. 9 to 11, a second embodiment of a percutaneous catheter of the present disclosure (which will hereinafter be referred to as a "catheter") will be described. FIG. 9 is a schematic plan view of a catheter of the second embodiment, FIG. 10 is a schematic front view of the catheter of the second embodiment, and FIG. 11 is a schematic cross-sectional view of the catheter of the second embodiment. FIG. 11 illustrates a set dilator used when the catheter is inserted.

In accordance with an exemplary embodiment, a catheter 60 is a so-called double lumen catheter, which can perform both blood feeding and blood removing at the same time. Therefore, in the present embodiment, in the external circulation device in FIG. 1, without using the vein side catheter (catheter for blood removing) 5 and the artery side catheter (catheter for blood feeding) 6, only the catheter 60 is inserted through a carotid artery N in the neck of the patient P.

After the catheter 60 is inserted, the distal end of the catheter 60 reaches the inferior vena cava, and a blood feeding port (connector 45-1 with a side hole) is directed toward a tricuspid valve of the right atrium.

In description of the catheter 60 in FIGS. 9 to 11, the same reference signs are applied to configurations in common with those of the catheter 30 of the first embodiment, and duplicated description will be invoked. Hereinafter, differences will be mainly described.

Similar to the first embodiment, since the first tube 32 has an increased inner diameter, the first tube 32 has an inner diameter, which is greater (or wider) than an inner diameter of the second tube 33.

The first tube 32 and the second tube 33 of the catheter 60 are connected to each other by a side hole connector 45-1.

As illustrated in FIG. 11, in the catheter 60, a first lock connector 36-1 and a second lock connector 36-2 are provided in a parallel manner. The first lock connector 36-1 is used for removing blood, and the second lock connector 36-2 is used for feeding blood. The two lock connectors 36-1 and 36-2 are connected to one catheter tube 31.

Lumens 61 and 62, which are divided from each other and serve as hollow liquid passing passages, are individually formed inside the second tube 33 of the catheter tube 31. Both the liquid passages (lumens 61 and 62) are divided in a liquid-tight manner and extend inside the second tube 33 in a parallel manner.

The first lock connector 36-1 is connected to the first lumen 61. The second lock connector 36-2 is connected to the second lumen 62.

In accordance with an exemplary embodiment, the first lumen 61 which is one liquid passing passage serving as a blood removing path passes through the inside of the second tube 33 and is connected to a side hole 63-1 of the side hole connector 45-1.

The second lumen 62 which is the other liquid passage serving as a blood feeding path passes through the inside of the first tube 32 and is connected to the distal tip 41.

The side hole connector 45-1 is connected to the first lumen 61 in a configuration different from that of the first embodiment. In accordance with an exemplary embodiment, through-hole 63-1 of the side hole connector 45-1 is a blood removing hole.

The structure of the distal tip 41 is the same as that in the first embodiment, except for being open for blood feeding.

The present embodiment is configured as described above, and the characterized first tube 32 exhibits the same function as that in the first embodiment and also has an operational effect in common.

Furthermore, the catheter 60 can be inserted with respect to a patient in the same manner as the catheter of the first embodiment by using the dilator 50 and the guide wire (not illustrated).

However, according to the second embodiment, it is possible to perform functions of both blood removing and liquid feeding with one catheter.

Incidentally, the present disclosure is not limited to the above-described embodiment and various changes can be made without departing from the scope of Claims. The above-described embodiment of the present disclosure can be combined in any manner. Each of the configurations in the embodiment can be partially omitted or can be combined in any manner to be different from that described above.

The detailed description above describes amelioration of a percutaneous catheter feeding blood. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A percutaneous catheter, comprising:
a catheter tube that includes a first tube and a second tube, the second tube configured to be in fluid communication with the first tube;
wherein the first tube has an inner diameter, the inner diameter of the first tube being greater than an inner diameter of the second tube, and wherein the first tube is more flexible than the second tube;
a distal tip gradually reduced in diameter toward a distal side, the distal tip configured to be fixed to a distal end of the first tube;
a connector having at least one side hole, the connector configured to connect a proximal end of the first tube to a distal end of the second tube; and
wherein the distal tip is provided with a blood removing hole and a flat butting portion configured to receive a distal portion of a dilator in a planar manner.

2. The percutaneous catheter according to claim 1, wherein the first tube is reinforced with a wire so as to realize a structure which is not blocked due to action of a negative pressure applied to the first tube, and when the first tube expands and contracts, the wire is configured to follow the expansion and contraction of the first tube.

3. The percutaneous catheter according to claim 1, wherein the second tube has a first lumen and a second lumen, the first and second lumens being divided lumens which are hollow liquid passing passages formed inside the second tube, the first lumen configured as a blood feeding path extending inside the first tube, and the second lumen configured as a blood removing path and connected to the at least one side hole of the connector.

4. The percutaneous catheter according to claim 1, wherein the distal tip has a tapered shape and a flat receiving surface on an inner side of the distal tip, the flat receiving surface being configured to be attached to a distal plane of the dilator prior to insertion of the catheter into a patient.

5. The percutaneous catheter according to claim 1, wherein the first and the second tubes are each reinforced with a wire mesh.

6. The percutaneous catheter according to claim 5, wherein the wire mesh is disposed on outer surface of the first and second tubes and a urethane coating is placed over the wire mesh of the first and second tubes.

7. The percutaneous catheter according to claim 1, wherein the first and the second tubes are each reinforced with a coiled shaped wire.

8. The percutaneous catheter according to claim 1, wherein the first tube is located distally of the second tube.

9. A percutaneous catheter, comprising:
a catheter tube that includes a first reinforced tube and a second reinforced tube, the second reinforced tube configured to be in fluid communication with the first reinforced tube, and wherein the first reinforced tube has an inner diameter, the inner diameter of the first reinforced tube being greater than an inner diameter of the second reinforced tube, and wherein the first reinforced tube is more flexible than the second reinforced tube;
a distal tip gradually reduced in diameter toward a distal side, the distal tip configured to be fixed to a distal end of the first tube;
a connector having at least one side hole, the connector configured to connect a proximal end of the first tube to a distal end of the second tube; and
wherein the distal tip is provided with a blood removing hole and a flat butting portion configured to receive a distal portion of a dilator in a planar manner.

10. The percutaneous catheter according to claim 9, wherein the first and the second reinforced tubes are reinforced with a wire mesh.

11. The percutaneous catheter according to claim 10, wherein the wire mesh is disposed on outer surface of the first and second reinforced tubes and a urethane coating is placed over the wire mesh of the first and second reinforced tubes.

12. The percutaneous catheter according to claim 10, wherein the first and the second reinforced tubes are each reinforced with a coiled shaped wire.

13. A method of using a percutaneous catheter through which blood passes, the percutaneous catheter being provided with a catheter tube that includes a first tube and a second tube configured to be in fluid communication with the first tube, the first tube having an inner diameter greater than an inner diameter of the second tube and the first tube being more flexible than the second tube, the method comprising:
inserting a dilator into a lumen of the catheter tube, the dilator configured to cause the first tube to expand in an axial direction, and causing an outer diameter of the first tube to be in smaller than the outer diameter without the dilator; and
advancing the percutaneous catheter with the dilator over a guide wire, the guide wire having been previously inserted into a patient to a catheter insertion site.

14. The method according to claim 13, comprising:
pulling the dilator and the guide wire from the catheter insertion site to a location of a clamping tube of the percutaneous catheter and clamping the dilator and the guide wire after the percutaneous catheter has been advanced to the catheter insertion site.

15. The method according to claim 14, wherein the percutaneous catheter comprises a blood feeding percutaneous catheter and a blood removing percutaneous catheter, the method further comprising
connecting a circulation circuit of an extracorporeal circulator to a connector of each of the blood feeding percutaneous catheter and the blood removing percutaneous catheter.

16. The method according to claim 15, further comprising:
removing an air bubble remaining inside each of the connectors of the blood feeding percutaneous catheter and the blood removing percutaneous catheter by using a syringe from a circulation circuit side.

17. The method according to claim 15, further comprising:
inserting the blood feeding percutaneous catheter through a femoral artery of the patient; and
inserting the blood removing percutaneous catheter through a femoral vein of the patient and indwelling a distal end of the blood removing percutaneous catheter in a right atrium of the patient.

18. The method according to claim 13, further comprising:
fixing a distal tip to a distal end of the first tube, the distal tip gradually reduced in diameter toward a distal side, the distal tip having a blood removing hole and a flat butting portion configured to receive a distal portion of a dilator; and connecting a proximal end of the first tube to a distal end of the second tube with a connector having at least one side hole.

19. The method according to claim 18, wherein the second tube has a first lumen and a second lumen, the first and second lumens being divided lumens which are hollow liquid passing passages formed inside the second tube, the first lumen configured as a blood feeding path extending inside the first tube, and the second lumen configured as a blood removing path and connected to the at least one side hole of the connector.

\* \* \* \* \*